United States Patent [19]

McWhorter et al.

[11] 4,044,757
[45] Aug. 30, 1977

[54] CHOLANGIOGRAPHY DEVICE AND METHOD

[75] Inventors: Daniel M. McWhorter, Arlington Heights; Bhupendra C. Patel, Elgin, both of Ill.

[73] Assignee: The Kendall Company, Boston, Mass.

[21] Appl. No.: 648,990

[22] Filed: Jan. 14, 1976

[51] Int. Cl.² .................. A61B 6/00; A61M 1/00
[52] U.S. Cl. .................... 128/2 A; 128/218 C; 128/218 PA; 128/234
[58] Field of Search ............. 128/2 A, 2 R, 214 R, 128/214 F, 218 R, 218 C, 234, 273, 218 PA

[56] References Cited

U.S. PATENT DOCUMENTS

| | | | |
|---|---|---|---|
| 1,696,018 | 12/1928 | Schellberg | 128/240 |
| 2,112,160 | 3/1938 | Johnson | 128/334 |
| 2,739,591 | 3/1956 | Yochem | 128/218 C |
| 3,399,668 | 9/1968 | Lundgren | 128/348 X |
| 3,888,239 | 6/1975 | Rubinstein | 128/2 A |
| 3,918,456 | 11/1975 | Patel | 128/348 |

FOREIGN PATENT DOCUMENTS 9,324  10/1902  Austria .................. 128/218 C

Primary Examiner—Dalton L. Truluck
Attorney, Agent, or Firm—Powell L. Sprunger

[57] ABSTRACT

A device for use in cholangiography and similar procedures comprising, a first syringe having a barrel defining a chamber for retaining an irrigation liquid, and a plunger having one end received in the chamber for pumping the liquid from the chamber. The device has a second syringe having a barrel defining a chamber for retaining a liquid contrast medium, and a plunger having one end received in the chamber of the second syringe for pumping the contrast medium from the chamber. The device has a catheter having a distal end, a proximal end, and a lumen extending through the catheter. The device also has means for connecting the proximal end of the catheter to the chambers of the first and second syringes without exposing the liquids to the atmosphere intermediate the lumen and chambers, in order that the irrigation liquid and contrast medium may be ejected through the catheter without introduction of air into the device.

3 Claims, 9 Drawing Figures

CHOLANGIOGRAPHY DEVICE AND METHOD

BACKGROUND OF THE INVENTION

The present invention relates to a device for use in cholangiography or silimar procedures.

Cholangiography may be defined as an X-ray of the biliary duct system of a patient to determine whether gall stones are present in the system. During cholecystectomy, i.e., surgical removal of the patient's gall bladder, the surgeon usually attempts to ascertain whether gall stones are present in the duct system, particularly the common bile duct, and thus must be removed. However, choledochotomy, i.e., the surgical incision of the common bile duct, should be avoided if stones are not present in the common duct, since this procedure, just as overlooked stones, may be a source of post-cholecystectomy morbidity. Thus, cholangiography should be performed before surgical intervention into the common duct to eliminate an unnecessary choledochotomy.

In the past, operative cholangiography has been most simply performed in the following manner. A syringe containing a saline solution is attached to a prioximal end of a catheter, an incision is made in the patient's cystic duct, which extends between the gall bladder and the common duct, and a distal end of the saline filled catheter is inserted through the incision and is positioned adjacent the juncture of the cystic duct and common duct. Next, the syringe plunger is depressed in order to irrigate the duct system with the saline solution, thus flushing the common duct to remove bile fluid, debris, and air, and to provide an indication that the common duct is not blocked. Normally, a relatively small quantity of saline solution is required to perform the irrigation procedure.

The irrigation syringe is then removed from the catheter, and another syringe containing a liquid contrast medium is attached to the proximal end of the catheter, after which the contrast medium is ejected from the catheter into the duct system. At this time, a cholangiogram, i.e., an X-ray, is obtained of the duct system, on which the stones appear as dark round shadows since they are less dense to the X-rays than the contrast medium. Additional cholangiograms are normally obtained while using increased quantities of the contrast medium.

Air bubbles, if present in the duct system during cholangiography, also appear as dark round shadows similar to stones on the cholangiograms. Hence, air must be prevented from entering the duct system during cholangiography, since the bubbles are likely to be interpreted as stones on the cholangiogram. In the past, the cholangiography devices offered an opportunity for air to enter the system when the syringes are changed. Thus, air bubbles may be injected into the duct system by the prior devices, and may result in an unnecessary and undesired choledochotomy attendant with loss of confidence in cholangiography by the surgeon when no stones are found during the choledochotomy.

SUMMARY OF THE INVENTION

A principal feature of the present invention is the provision of a device for performing cholangiography and similar procedures in an improved manner.

The device of the present invention comprises, a first syringe having a barrel defining a chamber for retaining an irrigation liquid, and a plunger having one end received in the chamber for pumping the liquid from the chamber. The device has a second syringe having a barrel defining a chamber for retaining a liquid contrast medium, and a plunger having one end received in the chamber of the second syringe for pumping the contrast medium from the chamber. The device has a catheter having a distal end, a proximal end, and a lumen extending through the catheter. The device also has means for connecting the proximal end of the catheter to the chambers of the first and second syringes without exposing the liquids to the atmosphere intermediate the lumen and chambers.

A feature of the present invention is that the irrigation liquid and contrast medium may be ejected through the catheter without introduction of air into the device.

Thus, a feature of the invention is that the device prevents injection of air bubbles into the duct system during cholangiography, and minimizes the possibility that a false indication of a stone will be obtained on a cholangiogram.

Another feature in an embodiment of the present invention is the provision of valve means for selectively connecting the proximal end of the catheter to the chambers of the first and second syringes.

A feature of the present invention is that the irrigation liquid and contrast medium may be separately ejected through the catheter, as controlled with the valve means, without introducing air into the device.

Yet another feature in an embodiment of the invention is the provision of a catheter having a double lumen, and means for connecting each of the lumens to separate chambers of the two syringes.

Thus, a feature of the invention is that the irrigation liquid and contrast medium may be ejected through separate lumens of the catheter without introducing air into the device.

Further features will become more fully apparent in the following description of the embodiments of this invention and from the appended claims.

DESCRIPTION OF THE PREFERRED EMBODIMENTS

Figure 1:
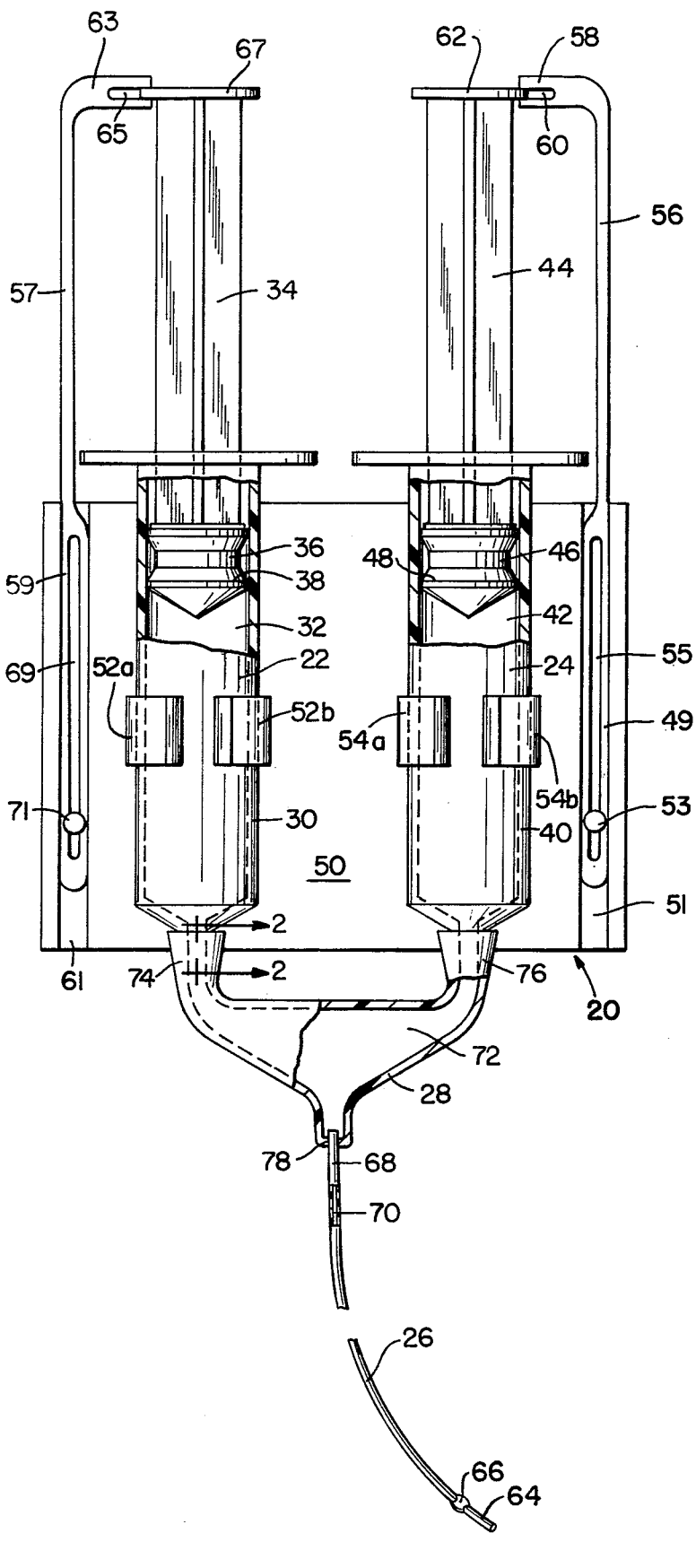
FIG. 1 is a fragmentary elevational view, taken partly in section, of a device of the present invention for performing cholangiography and related procedures.

Referring now to FIG. 1, there is shown a device generally designated 20 having a first syringe 22, a second syringe 24, a catheter 26, and a Y-shaped connector or adapter 28. As will be further discussed below, the device 20 is utilized to eject an irrigation liquid and a liquid radiopaque contrast medium from the catheter during cholangiography or similar procedure on a patient.

The first syringe 22 has a barrel 30 defining a chamber 32 for retaining the irrigation liquid, such as a saline solution. The first syringe 22 also has a plunger 34 having one end 36 containing a flexible plug 38 received in the chamber 32 of the first syringe 22. The plunger 34 is pushed into the syringe chamber 32 to eject the irrigation liquid from the first syringe.

The second syringe 24 has a barrel 30 defining a chamber 42 for retaining the liquid contrast medium of known type which is opaque to X-rays. The second syringe 24 also has a plunger 44 having one end 46 containing a flexible plug 48 received in the chamber 42 of the syringe. The liquid contrast medium is ejected from the second syringe 24 by pushing the plunger 44 into the syringe chamber.

The device 20 may have a plate 50 for retaining the first and second syringes 22 and 24 in a generally aligned configuration. As shown, the plate or retaining member has a pair of flexible clips 52a and 52b to receive and retain the first syringe 22 at its desired position on the plate 50. The plate 50 also has a pair of flexible clips 54a and 54b to receive and retain the second syringe 24 at its desired position on the plate 50.

The device 20 may have means for releasably locking the plunger 44 of the second syringe 24 at a selected adjustable position. In the particular embodiment shown, the locking means comprises a flexible arm 56 having an end portion 49 slidably received in an elongated groove 51 of the plate 50, and having an inwardly directed locking member 58. The locking member 58 has a groove 60 adjacent its inner end to receive an outwardly directed flange 62 on the plunger 44 adjacent its outer end. The arm 56 is flexed outwardly in order to release the plunger flange 62 from the groove 60 of the locking member 58, and permit movement of the plunger 44 into the chamber 42 of the second syringe 24. As shown, the end portion 49 of the arm 56 has an elongated slot 55 to receive a thumbscrew 53 which is threaded into the plate 50. Thus, the arm end portion 49 may be moved to a desired position longitudinally in the groove 51 and may be secured in place by the thumbscrew 53, in order to releasably lock the plunger 44 of the second syringe 24 at a selected position.

The device 20 also has means for releasably locking the plunger 34 of the first syringe 22 at a selected adjustable position. The locking means comprises a flexible arm 57 having an end portion 59 slidably received in an elongated groove 61 of the plate 50, and having an inwardly directed locking member 63. The locking member 63 has a groove 65 adjacent its inner end to receive an outwardly directed flange 67 on the plunger 34 adjacent its outer end. In a manner as previously described in connection with the locking means of the second syringe 24, the arm 57 may be flexed outwardly in order to release the plunger flange 67 from the groove 65 of the locking member 63, and permit movement of the plunger 34 into the chamber 32 of the first syringe 22. Also, the end portion 59 of the arm 57 has an elongated slot 69 to receive a thumbscrew 71 which is threaded into the plate 50. Accordingly, the arm end portion 59 may be moved to a desired position longitudinally in the groove 61 and may be secured in place by the thumbscrew 71, such that the plunger 34 of the first syringe 22 is releasably locked at a selected position.

The catheter 26 has a distal end 64 for placement in the patient, a proximal end 68, and a lumen 70 extending between the distal and proximal ends 64 and 68 of the catheter 26. The catheter 26 may also have an outer bead 66 spaced slightly from the distal end 64 of the catheter 26 for a purpose which will be described below.

Figure 2:
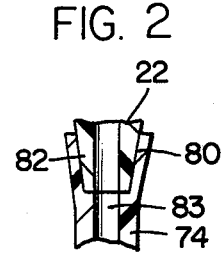
FIG. 2 is a fragmentary sectional view taken substantially as indicated along the line 2—2 of FIG. 1.

The connector 28 has a cavity 72 which communicates with the chamber 32 of the first syringe 22 through a first conduit portion 74, and which communicates with the chamber 42 of the second syringe 24 through a second conduit portion 76. As shown, the connector 28 also has an opening 78 to receive the proximal end 68 of the catheter 26, such that the lumen 70 of the catheter 26 communicates through the cavity 72 of the connector 28 with the chambers 32 and 42 of the first and second syringes 22 and 24, respectively. The first and second conduit portions 74 and 76 of the connector 28 may be attached to the first and second syringes 22 and 24 by any suitable means. For example, as illustrated in FIG. 2 in connection with the first syringe 22, the first conduit portion 74 may have a recess 80 to releasably receive the tip 82 of the first syringe 22, such that the syringe chamber communicates through the tip 82 with a channel 83 in the first conduit portion 74. The tip of the second syringe 24 may be connected to the second conduit portion 76 of the connector 28 in a similar fashion.

Figure 3:
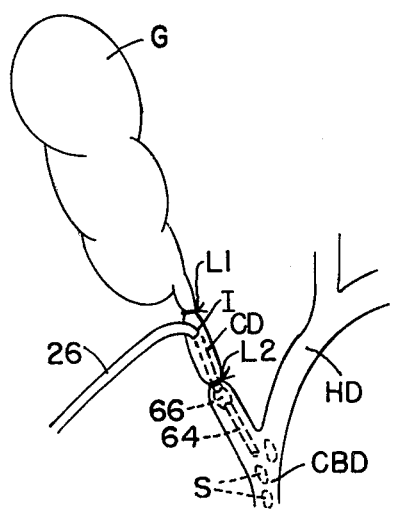
FIG. 3 is a diagrammatic view showing a catheter of the device of FIG. 1 in position for performing cholangiography.

The use of the device for performing cholangiography will be described in connection with FIGS. 1 and 3. First, the chamber 32 of the first syringe 22 is filled with the irrigation liquid, and the chamber 42 of the second syringe 24 is filled with the liquid contrast medium either before or after attachment of the syringes to the plate 50. The connector 28 is then attached to the tips of the syringes, and the device 20 is inverted to place the connector 28 in an upright position above the syringes. The plungers 34 and 44 of the first and second syringes 22 and 24, respectively, are then pressed into the syringe chambers to pump a small quantity of the liquids through the connector 28 and the catheter while removing any air from the device. After the plunger 44 of the second syringe 24 has been depressed a sufficient amount to expel air from the device, the position of the arm 56 and associated locking member 58 may be adjusted through use of the thumbscrew 53 to lock the plunger 44 in place.

During cholangiography, the surgeon places a ligature L1 around the cystic duct CD adjacent the gall bladder G, and makes an incision I in the cystic duct CD, as shown. Next, the distal end 64 of the catheter 26 is passed through the incision I and the cystic duct CD until the distal end 64 of the catheter 26 is positioned adjacent the juncture of the common bile duct CBD, the hepatic duct HD, and the cystic duct CD, after which a ligature L2 is placed around the cystic duct CD proximal the catheter bead 66 in order to retain the catheter 26 at the desired position. The surgeon may then eject the irrigation liquid from the catheter 26 into the duct system by pressing the plunger 34 of the first syringe 22 into the syringe chamber 32. The irrigation liquid serves to flush out the duct system, while determining whether the common duct CBD permits passage of liquid and is not blocked. During the irrigation procedure, the locking member 58 retains the plunger 44 of the second syringe 24 at the selected position, and minimizes mixing of the irrigation liquid with the contrast medium in the chamber 42 of the second syringe 24.

After the irrigation procedure has been completed, the position of the arm 57 and associated locking member 63 may be adjusted through use of the thumbscrew 71 to lock the plunger 34 of the first syringe 22 in place. Next, the surgeon may release the locking member 58 from the plunger flange 62, and the plunger 44 of the second syringe 24 may be pushed into the chamber 42 of the second syringe 24 to eject a quantity of contrast medium from the catheter 26 into the biliary duct system. At this time, an X-ray is taken of the duct system in order to obtain a cholangiogram and determine whether any stones S are present which should be removed. Normally, this procedure is repeated two more times, with additional quantities of the contrast medium being pumped into the duct system, in order to obtain additional cholangiograms. During this time, the locking member 63 retains the plunger 34 of the first syringe 22 at the selected position, and minimizes mixing of the contrast medium with the remaining irrigation liquid in the chamber 32 of the first syringe 22.

Thus, according to the present invention the irrigation liquid and contrast medium are pumped through the catheter 26 while maintaining the proximal end 68 of the catheter 26 closed to the atmosphere, in order to prevent passage of air bubbles into the duct system during cholangiography. Since such air bubbles would be similar in appearance to a gall stone on a cholangiogram, the device of the present invention minimizes the possibility that confusion may arise from a false indication of a stone in the duct system on the cholangiogram, thus preventing an unnecessary and undesired incision of the common duct CBD.

Figure 4:
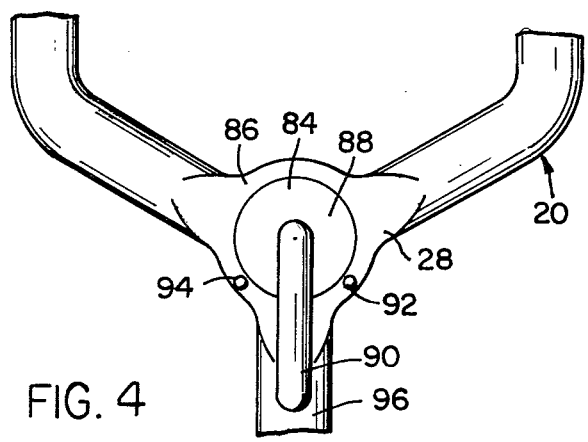
FIG. 4 is a fragmentary plan view of a valve in a connector for the device of FIG. 1.

Another embodiment of the device of the present invention is illustrated in FIGS. 4–7, in which like reference numerals designate like parts. In this embodiment, the connector 28 includes a valve 84 for selectively connecting the catheter to the chambers of the first and second syringes. The valve 84 has a valve housing 86, and a valve member 88 rotatably mounted in the valve housing 86. Referring to FIG. 4, the valve 84 has a handle 90 extending from the outside of the valve member 88 to facilitate rotation of the valve member 88 in the housing 86. The valve housing 86 has a pair of bosses 92 and 94 which serve as stops to limit rotational movement of the valve member 88 in the valve housing 86. Thus, the handle 90 of the valve member 88 strikes the boss 92 at a first rotational position of the valve member 88, while the handle 90 strikes the boss 94 at a second rotational position of the valve member 88, such that the bosses 92 and 94 limit movement of the handle 90 and valve member 88 between the first and second rotational positions.

Figure 5:
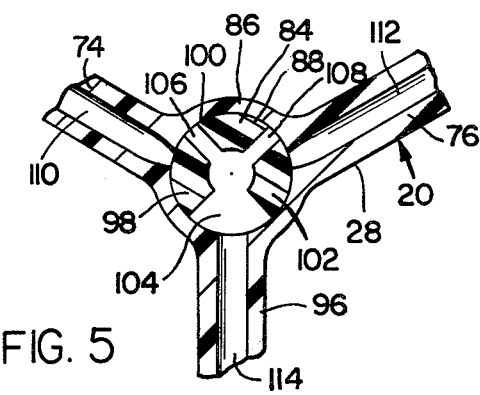
FIGS. 5-7 are fragmentary sectional views of the valve of FIG. 4 showing a valve member in the valve at different rotational positions.

As illustrated in FIGS. 4 and 5, the handle 90 is aligned with a third conduit 96, which is connected to the proximal end of the catheter, at a third rotational position of the valve member 88 intermediate the first and second rotational positions. As shown in FIG. 5, the valve member 88 has first, second, and third wall sections 98, 100, and 102, respectively, defining an enlarged opening 104 and first and second passageways 106 and 108, respectively, in the valve member 88. As shown, the opening 104 and first and second passageways 106 and 108 communicate with each other in the valve member 88, and extend to the outside of the valve member 88. When the handle 90 and valve member 88 are located at the third intermediate rotational position, the first wall section 98 of the valve member 88 blocks a channel 110 in the first conduit portion or conduit 74 which communicates with the first syringe chamber, and the third wall section 102 blocks a channel 112 in the second conduit portion or conduit 76 which communicates with the second syringe chamber. Thus, in this configuration of the valve member 88, the valve 84 prevents passage of liquid from both of the syringes through the connector 28.

Figure 6:
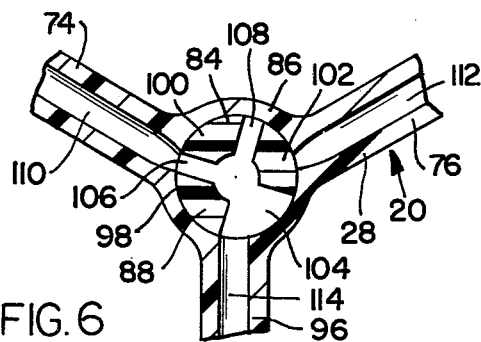
Figure 7:
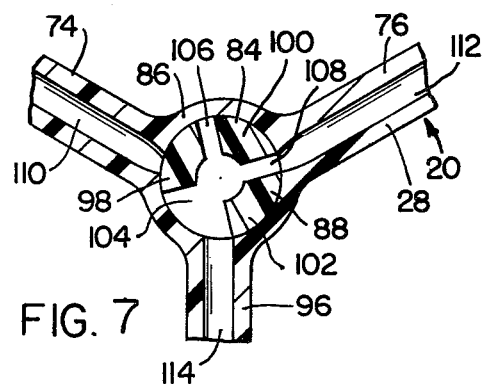

Referring to FIG. 6, when the handle 90 and valve member 88 are moved to the first rotational position, the first passageway 106 of the valve member 88 is aligned with the channel 110 of the first conduit 74. Thus, in this configuration of the valve member 88, the irrigation liquid may be ejected from the first syringe through the channel 110 of the first conduit 74, the passageway 106 of the valve member 88, the opening 104 of the valve member 88, and into a channel 114 of the third conduit 96, after which the irrigation liquid passes through the catheter, as previously described. With reference to FIG. 7, when the handle 90 and valve member 88 are located at their second rotational position in the housing 86, the passageway 108 of the valve member 88 is aligned with the channel 112 of the second conduit 76, such that the liquid contrast medium may be ejected through the passageway 112 of the second conduit 76, the passageway 108 of the valve member 88, the opening 104 of the valve member 88, the channel 114 of the third conduit 96, and into the catheter. Accordingly, the opening 104 is aligned with the channel 114 of the third conduit 96 at all three rotational positions of the valve member 88 in the housing 86, while the passageway 106 is aligned with channel 110 of the first conduit 74 at the first rotational position of the valve member 88, and the passageway 108 is aligned with the channel 112 of the second conduit 76 at the second rotational position of the valve member 88.

In use of the device of FIGS. 4–7, after the respective syringe chambers have been filled with the irrigation liquid and the liquid contrast medium, the valve member 88 may be moved to its second rotational position, after which the plunger in the second syringe is pressed into the syringe chamber to eject a small quantity of contrast medium through the catheter and remove any air which may be present in the chamber of the second sryinge or the second conduit 76. Next, the valve member 88 may be moved to its first rotational position, after which the plunger of the first syringe may be pushed into the syringe chamber to eject irrigation liquid through the catheter and remove any air which may be present in the chamber of the first syringe or the first conduit 74. At this time, the catheter has been filled with the irrigation liquid, and air has been removed from the device. If desired, the valve member 88 may then be moved to its third rotational position to prevent passage of liquid through the valve 84 until the device is ready for use.

After the distal end of the catheter has been secured in the cystic duct of the patient, the valve member 88 is positioned at its first rotational position, and the irrigation liquid is ejected from the first syringe through connector 28 and the catheter into the duct system of the patient. After the irrigation procedure has been completed, the valve member 88 is moved to its second rotational position, and the liquid contrast medium is ejected from the second syringe through the connector 28 and the catheter into the duct system of the patient in order to obtain a cholangiogram of the duct system. As before, the irrigation liquid and contrast medium are ejected from the device without introducing air bubbles into the device or the duct system, in order to prevent a false indication of a stone on the cholangiogram.

Figure 9:
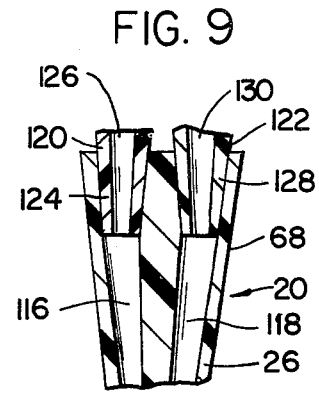
FIG. 9 is a fragmentary sectional view on an enlarged scale showing a connecting portion of the device of FIG. 8.
Figure 8:
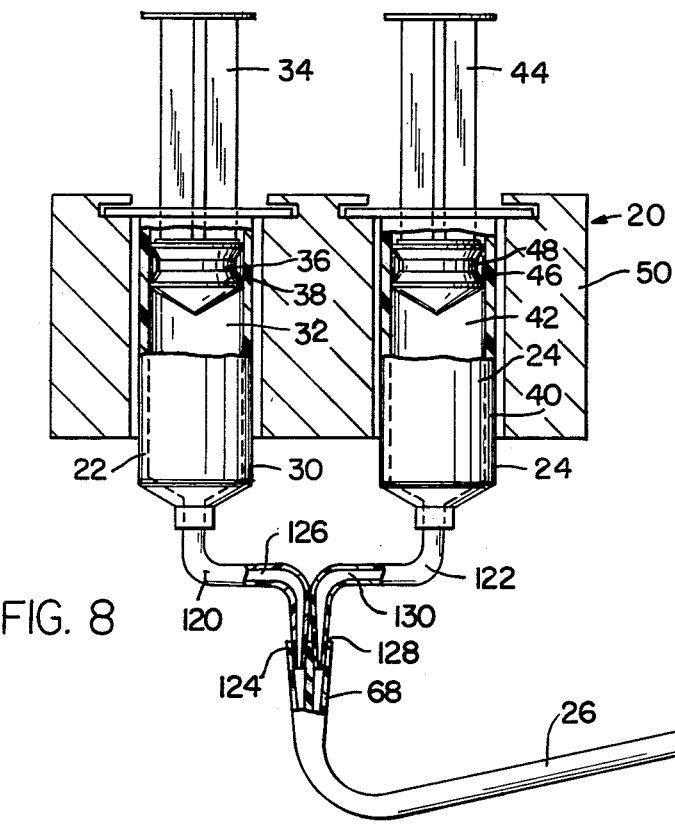
FIG. 8 is a fragmentary elevational view, taken partly in section, of another embodiment of the device of the present invention.

Another embodiment of the device 20 of the present invention is illustrated in FIGS. 8 and 9, in which like reference numerals designate like parts. The first and second syringes 22 and 24 may be connected to a suitable plate or retaining member 50 in a manner as previously described in connection with the device of FIG. 1. In this embodiment, the catheter 26 has a pair of first and second lumens 116 and 118 extending between the proximal end 68 and distal end 64 of the catheter 26, and the catheter 26 may be connected to the syringes 22 and 24 by a pair of first and second conduits 120 and 122. The first conduit 120 has a distal end 124 received in the proximal end portion of the first catheter lumen 116, such that a lumen 126 of the first conduit 120 communicates between the first catheter lumen 116 and the chamber 32 of the first syringe 22. The second conduit 122 also has a distal end 128 received in a proximal end portion of the second catheter lumen 118, such that a lumen 130 of the second conduit 122 communicates between the second catheter lumen 118 and the chamber 42 of the second syringe 24. The first and second conduits 120 and 122 may be attached by any suitable means to the first and second syringes 22 and 24, and, if desired, a body member may be provided of suitable type to retain the distal end portions 124 and 128 of the first and second conduits 120 and 122 together.

In use of the device 20 of FIGS. 8 and 9, the plunger 34 of the first syringe 22 may be pushed slightly into the chamber 32 of the first syringe 22, in order to eject a small quantity of irrigation liquid through the first conduit 120 and the first lumen 116 of the catheter 26 and remove any air which may be in the chamber of the first syringe 22, the first conduit 120, or the first lumen 116 of the catheter 26. Next, the plunger 44 of the second syringe 24 may be pushed slightly into the chamber of the second syringe in order to eject a small quantity of liquid contrast medium through the second conduit 122 and the second lumen 118 of the catheter 26 and remove any air which may be in the chamber of the second syringe 24, the second conduit 122, or the second lumen 118 of the catheter 26. After the distal end 64 of the catheter 26 has been secured in place in the cystic duct of the patient, the plunger 34 of the first syringe 22 is pushed into the syringe 32 in order to eject irrigation liquid through the first lumen 116 of the catheter 26 and flush the duct system of the patient. After the irrigation procedure has been completed, the plunger 44 of the second syringe 24 is pushed into the chamber 42 of the second syringe 24, in order to eject liquid contrast medium through the second conduit 122 and the second lumen 118 of the catheter 26 into the duct system of the patient, after which a cholangiogram is obtained. In this manner, the irrigation liquid and contrast medium are pumped from the device through separate lumens 116 and 118 of the catheter 26 without introducing air into the device or the duct system of the patient, thus preventing a false indication of a stone in the common duct on the cholangiogram.

The foregoing detailed description is given for clearness of understanding only, and no unnecessary limitations should be understood therefrom, as modifications will be obvious to those skilled in the art.

We claim:

1. A device for use in cholangiography and similar procedures, comprising:
    a first syringe having a barrel defining a chamber for retaining an irrigation liquid, and a plunger having one end received in said chamber for pumping the liquid from said chamber;
    a second syringe having a barrel defining a chamber for retaining a liquid contrast medium, and a plunger having one end received in the chamber of the second syringe for pumping the contrast medium from said chamber;
    a catheter having a distal end, a proximal end, and a lumen extending through the catheter;
    means for connecting the proximal end of said catheter to the chambers of the first and second syringes without exposing the liquids to the atmosphere intermediate the lumen and chambers, whereby the irrigation liquid and contrast medium may be ejected through the catheter without introduction of air into the device; and
    a plate, said syringes being secured to said plate, a pair of elongated arms each having one end secured to said plungers and the other ends being slotted and slidably secured to said plate, screws secured to said plate and positioned in said slots to releasably lock said arms to in turn lock said plungers at any inner or outer selected position.

2. The device of claim 1 wherein the connecting means selectively connects the proximal end of the catheter to the chambers of said first and second syringes.

3. The device of claim 1 wherein said catheter has an outer bead spaced slightly from the distal end of the catheter.

* * * * *